(12) United States Patent
Chang et al.

(10) Patent No.: US 11,622,857 B2
(45) Date of Patent: Apr. 11, 2023

(54) BALLOON EXPANDABLE TRANSCATHETER VALVE DEPLOYMENT DEVICES AND METHODS

(71) Applicant: MEDTRONIC, INC., Minneapolis, MN (US)

(72) Inventors: William Chang, Santa Rosa, CA (US); James Mitchell, Windsor, CA (US); Leonila Rivera, Windsor, CA (US); Siyan Som, Fulton, CA (US); Martha Barajas-Torres, Santa Rosa, CA (US); Leo Mendoza, Santa Rosa, CA (US)

(73) Assignee: Medtronic, Inc., Minneapolis, MN (US)

( * ) Notice: Subject to any disclaimer, the term of this patent is extended or adjusted under 35 U.S.C. 154(b) by 406 days.

(21) Appl. No.: 16/892,545

(22) Filed: Jun. 4, 2020

(65) Prior Publication Data
US 2020/0383780 A1 Dec. 10, 2020

Related U.S. Application Data

(60) Provisional application No. 62/858,552, filed on Jun. 7, 2019.

(51) Int. Cl.
*A61F 2/24* (2006.01)
(52) U.S. Cl.
CPC .......... *A61F 2/2433* (2013.01); *A61F 2/2436* (2013.01)
(58) Field of Classification Search
None
See application file for complete search history.

(56) References Cited

U.S. PATENT DOCUMENTS

| | | | | |
|---|---|---|---|---|
| 5,843,116 A | * | 12/1998 | Crocker | A61M 25/1002 606/108 |
| 6,136,011 A | * | 10/2000 | Stambaugh | A61F 2/958 604/101.02 |
| 2001/0000350 A1 | * | 4/2001 | Durcan | A61F 2/958 623/1.11 |
| 2001/0007956 A1 | * | 7/2001 | Letac | A61F 2/2409 623/2.11 |
| 2003/0114913 A1 | * | 6/2003 | Spenser | A61F 2/2427 623/2.14 |
| 2004/0102791 A1 | | 5/2004 | Murray, III | |
| 2005/0209674 A1 | | 9/2005 | Kutscher et al. | |

(Continued)

OTHER PUBLICATIONS

International Search Report (ISA/210) for International Patent Application No. PCT/US2020/036122 issued/mailed by the European Patent Office dated Nov. 11, 2020.

(Continued)

*Primary Examiner* — Shaun L David
(74) *Attorney, Agent, or Firm* — Medler Ferro Woodhouse & Mills PLLC

(57) ABSTRACT

A catheter based balloon enabled prosthetic heart valve delivery device is provided. The balloon enabled delivery device is configured to deploy a prosthetic heart valve through inflation. The balloon enabled delivery device is further configured to reduce or prevent migration of the prosthetic heart valve during deployment. Migration is prevented through a combination of balanced inflation of the balloon, inflation fluid flow balancing structures, retention rings, retention covers, and balloon surface treatments.

20 Claims, 15 Drawing Sheets

(56) References Cited

U.S. PATENT DOCUMENTS

| | | | |
|---|---|---|---|
| 2006/0004439 A1* | 1/2006 | Spenser | A61F 2/2436 623/2.11 |
| 2006/0004442 A1* | 1/2006 | Spenser | A61F 2/2433 623/1.21 |
| 2006/0135985 A1 | 6/2006 | Cox et al. | |
| 2006/0235509 A1* | 10/2006 | Lafontaine | A61F 2/2436 623/2.14 |
| 2007/0005131 A1* | 1/2007 | Taylor | A61F 2/2427 623/2.11 |
| 2007/0027534 A1* | 2/2007 | Bergheim | A61F 2/2418 623/2.11 |
| 2007/0112422 A1* | 5/2007 | Dehdashtian | A61F 2/2433 623/2.11 |
| 2007/0293942 A1* | 12/2007 | Mirzaee | A61F 2/2418 623/2.11 |
| 2008/0021546 A1* | 1/2008 | Patz | A61F 2/2433 623/2.11 |
| 2009/0281609 A1* | 11/2009 | Benichou | A61F 2/2418 623/1.26 |
| 2009/0281619 A1* | 11/2009 | Le | A61M 25/0147 623/2.11 |
| 2011/0144742 A1* | 6/2011 | Madrid | A61F 2/2433 623/2.11 |
| 2011/0190867 A1* | 8/2011 | Vonderwalde | A61F 2/915 623/1.11 |
| 2012/0136200 A1* | 5/2012 | Miraki | A61F 2/2427 600/37 |
| 2013/0030519 A1 | 1/2013 | Tran et al. | |
| 2013/0030520 A1* | 1/2013 | Lee | A61F 2/958 623/2.11 |
| 2016/0082230 A1* | 3/2016 | McGhie | A61F 2/958 623/1.12 |
| 2016/0331534 A1 | 11/2016 | Buchbinder et al. | |
| 2017/0079793 A1* | 3/2017 | Maimon | A61F 2/2418 |
| 2018/0214267 A1 | 8/2018 | Lally et al. | |

OTHER PUBLICATIONS

Written Opinion of the International Searching Authority (ISA/237) for International Patent Application No. PCT/JS2020/036122 issued/mailed by the European Patent Office dated Nov. 11, 2020.

* cited by examiner

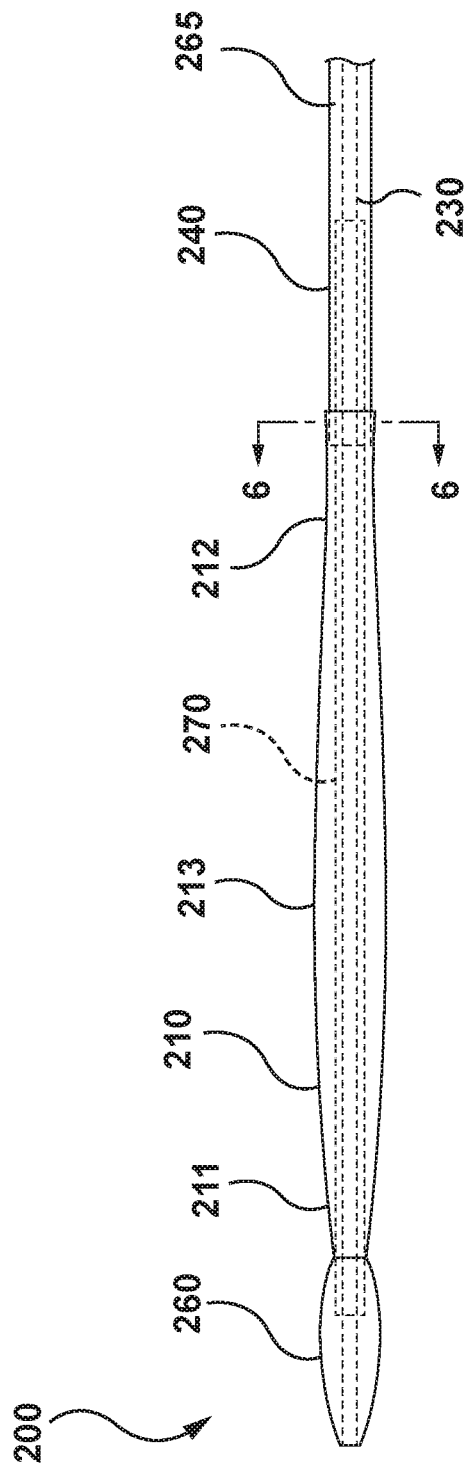
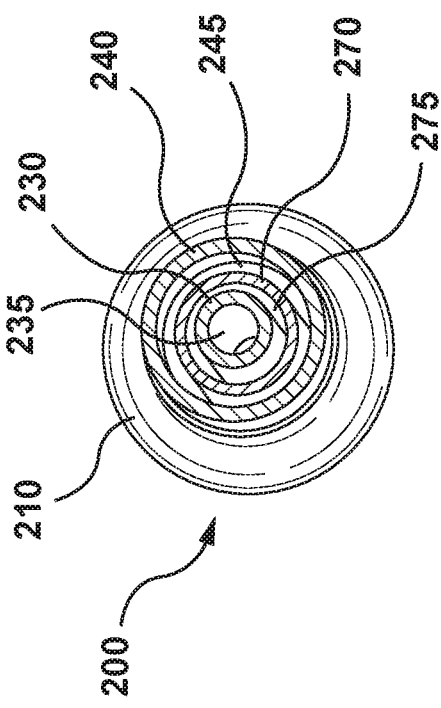
FIG. 5
FIG. 6

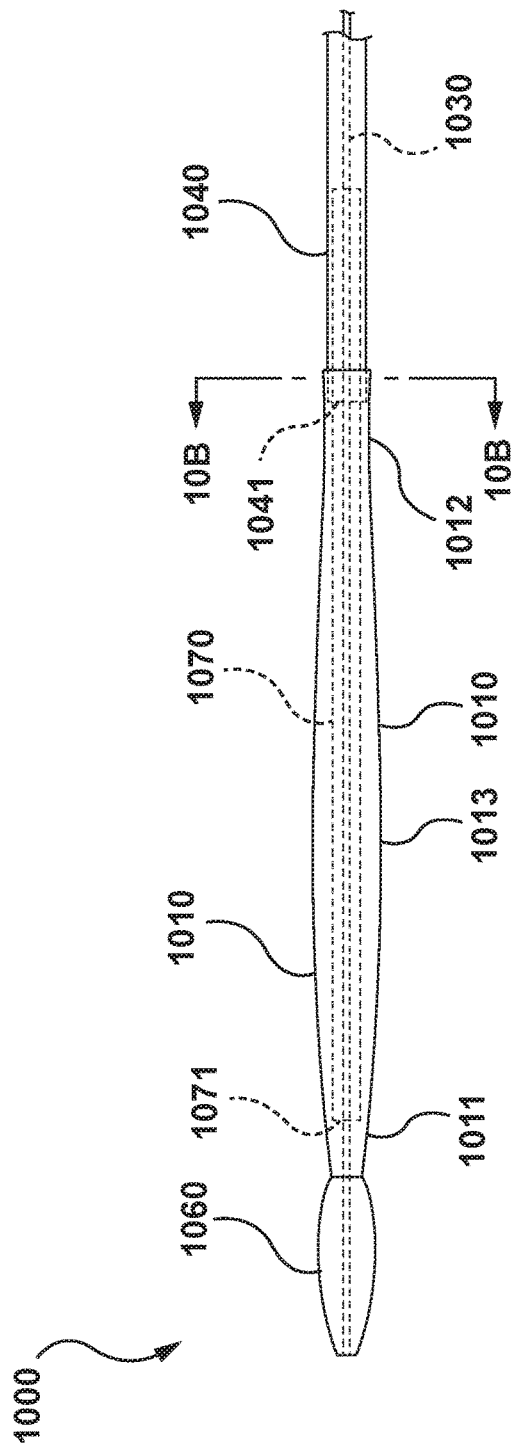
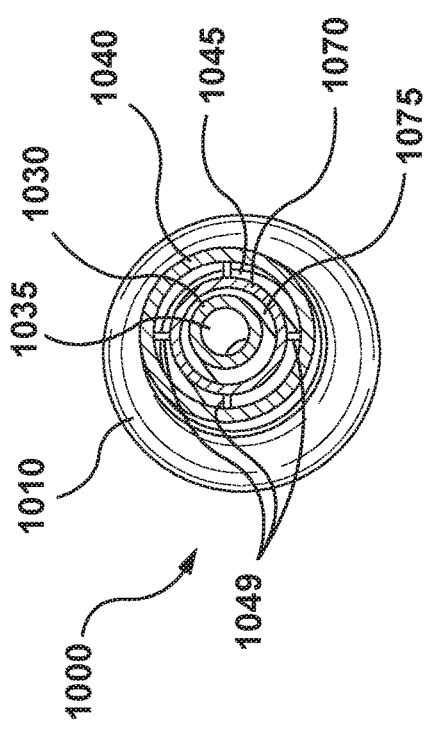
FIG. 10A
FIG. 10B

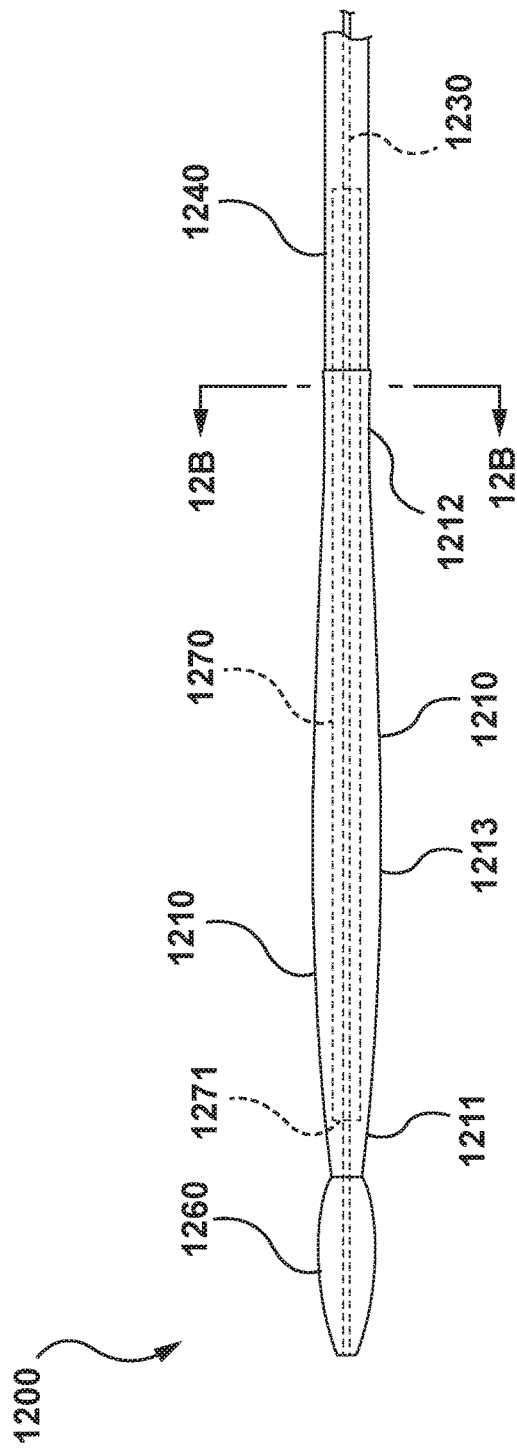
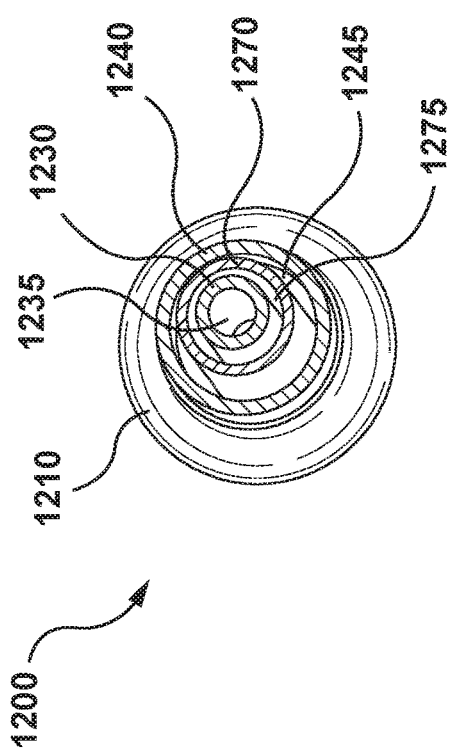
FIG. 12A
FIG. 12B

BALLOON EXPANDABLE TRANSCATHETER VALVE DEPLOYMENT DEVICES AND METHODS

RELATED MATTERS

This application claims priority under 35 USC § 119 to U.S. Provisional Application Ser. No. 62/858,552 filed on Jun. 7, 2019, the entire contents of which are incorporated herein by reference.

FIELD OF THE INVENTION

The present invention is related to systems and methods for transcatheter valve deployment. In particular, the present invention is related to balloon expandable delivery devices configured for the deployment of prosthetic heart valves.

BACKGROUND

Transcatheter valve technology provides a minimally invasive means of implanting prosthetic heart valves. The prosthetic heart valve is loaded onto a delivery system that is able to access and navigate the vasculature to the intended implant location and implant the valve. A conventional approach for a transcatheter valve device is to use a balloon catheter for the delivery system and a prosthetic valve incorporating a balloon expandable frame. After reaching the delivery site, the balloon is inflated to expand the prosthetic heart valve into a deployment configuration. After deployment, the balloon is deflated and the delivery catheter is removed. A problem that may be encountered in the use of conventional balloon catheter delivery devices is that of prosthetic heart valve migration during deployment. As the balloon is inflated, the valve may migrate proximally or distally from an original position on the catheter, making accurate positioning more difficult.

Devices and methods disclosed herein address the issue of prosthetic heart valve migration during deployment.

SUMMARY

Embodiments of the present invention relate generally to delivery devices for prosthetic heart valves, and, more specifically, to balloon enabled prosthetic heart valve delivery devices. Balloon enabled prosthetic heart valve delivery devices consistent with embodiments hereof are configured to reduce or prevent valve migration during deployment.

In an embodiment, a balloon enabled delivery device for deploying a prosthetic heart valve through balloon inflation is provided. The balloon enabled delivery device includes an inner shaft defining a guidewire lumen; an outer shaft surrounding the inner shaft defining an inflation lumen between the outer shaft and the inner shaft; and a balloon disposed at a distal end of the outer shaft such that fluid delivered to the balloon via the inflation lumen causes the balloon to inflate, the balloon having a proximal portion extending proximal to a crimping location of the prosthetic heart valve, a distal portion extending distally to the crimping location, and a central portion located within the crimping location, and being configured to inflate in a first stage during which the proximal portion and the distal portion of the balloon inflate to lock an axial position of the prosthetic heart valve, and inflate in a second stage during which the central portion of the balloon inflates to expand the prosthetic heart valve.

In another embodiment, a method of deploying a prosthetic heart valve through balloon inflation of a balloon enabled delivery device is provided. The method includes advancing the prosthetic heart valve along a guidewire to a deployment site, the guidewire being inserted into a guidewire lumen defined by an inner shaft of the balloon enabled delivery device; delivering fluid to a balloon of the balloon enabled delivery device via an outer shaft surrounding the inner shaft and defining an inflation lumen between the outer shaft and the inner shaft; inflating a proximal portion of the balloon extending proximal to a crimping location of the prosthetic heart valve and a distal portion of the balloon extending distally to the crimping location to lock an axial position of the prosthetic heart valve; inflating a central portion of the balloon located within the crimping location of the prosthetic heart valve to expand the prosthetic heart valve; completing inflation of the balloon to complete expansion of the prosthetic heart valve; and deflating the balloon.

BRIEF DESCRIPTION OF THE DRAWINGS

The accompanying figures, which are incorporated herein, form part of the specification and illustrate embodiments of a prosthesis delivery system. Together with the description, the figures further explain the principles of and enable a person skilled in the relevant art(s) to make and use the expandable balloon delivery devices described herein. In the drawings, like reference numbers indicate identical or functionally similar elements.

FIG. 5 is a plan view showing aspects of an expandable balloon delivery device according to embodiments hereof.

FIG. 6 is a cross-sectional view showing aspects of an expandable balloon delivery device according to embodiments hereof.

FIGS. 10A-10B illustrate an expandable balloon delivery device according to embodiments hereof.

FIGS. 12A-12B illustrate an expandable balloon delivery device according to embodiments hereof.

DETAILED DESCRIPTION OF THE INVENTION

Specific embodiments of the present invention are now described with reference to the figures. Unless otherwise indicated, for the delivery device and prosthetic heart valves described herein, the terms "distal" and "proximal" are used in the following description with respect to a position or direction relative to the treating clinician or operator. "Distal" and "distally" are positions distant from or in a direction away from the clinician, and "proximal" and "proximally" are positions near or in a direction toward the clinician.

The following detailed description is merely illustrative in nature and is not intended to limit the invention or the application and uses of the invention. Although the description of the invention is in the context of balloon enabled deployment of prosthetic valves, aspects of the invention may also be used in any other context that is useful. As an example, the description of the invention is in the context of deployment of prosthesis. As used herein, "prosthesis" or "prostheses" may include any prosthesis including a balloon expandable structure. Modifications can be made to the embodiments described herein without departing from the spirit and scope of the present invention. Therefore, the following detailed description is not meant to be limiting. Furthermore, there is no intention to be bound by any expressed or implied theory presented in the preceding technical field, background, summary, or the following detailed description.

Expandable balloon delivery devices consistent with embodiments hereof are configured to deliver and deploy, through the use of an inflatable balloon, transcatheter balloon expandable prosthetic heart valves (referred to herein as "prosthetic heart valves"). Transcatheter balloon expandable prosthetic heart valves are crimped onto the balloon of the delivery system. The balloon of the delivery system is processed such that the balloon is pleated then folded prior to crimping the prosthetic heart valve. The prosthetic heart valve is deployed by inflating the balloon which thereby radially expands the prosthetic heart valve. Unequal radial expansion of the prosthetic heart valve can lead to the prosthetic heart valve migrating during balloon inflation. Movement of the prosthetic heart valve may lead to an inaccurate deployment position and possibly under-deployed prosthetic heart valve. Challenges impacting valve migration during deployment include differential radial stiffness of the prosthetic heart valve across the prosthetic heart valve length and diminished fluid flow through the folded balloon. Embodiments hereof, as described below, serve to reduce or prevent prosthetic heart valve migration during deployment.

Figure 1:
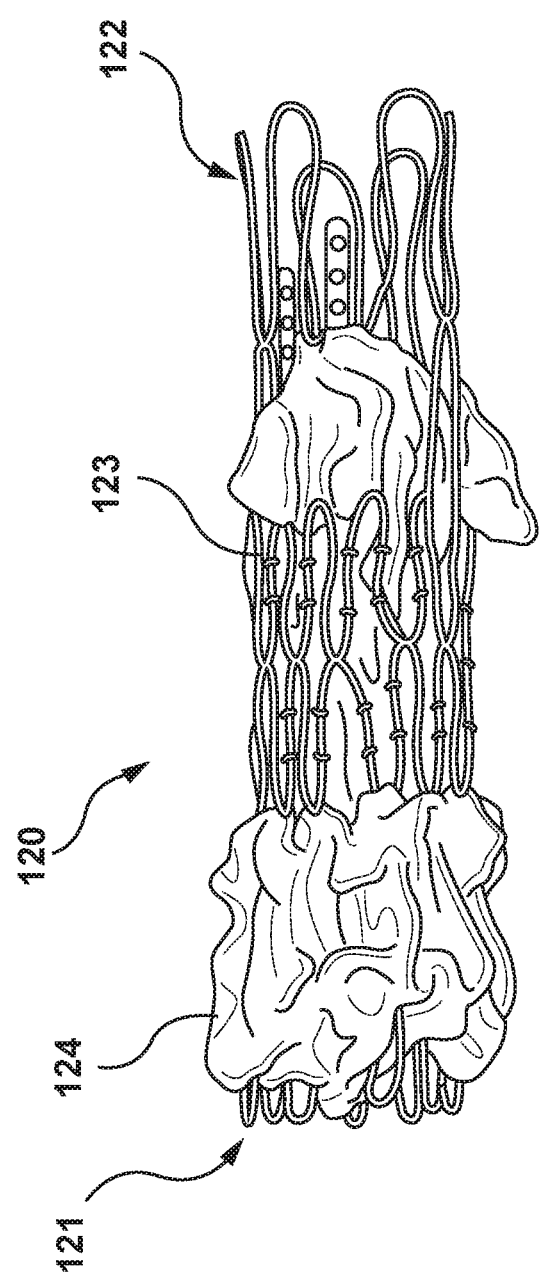
FIG. 1 illustrates a prosthetic heart valve and its associated balloon expandable frame and prosthetic valve tissue.

FIG. 1 illustrates a prosthetic heart valve 120 and its associated balloon expandable frame 123 and prosthetic valve tissue 124. The prosthetic heart valve 120 is configured for delivery by an expandable balloon delivery device. The prosthetic heart valve 120 has a proximal end 122 and a distal end 121. Prosthetic heart valve 120 is non-symmetrical, having different expandable frame 123 geometry and prosthetic valve tissue 124 construction at the proximal end 122 and the distal end 121. Other prosthetic heart valves may differ in design, having expandable frames that differ in structure and construction and prosthetic valve elements that also differ. Accordingly, different prosthetic heart valves may react differently under balloon expansion deployment, due to variations in structural characteristics, such as radial stiffness. Because different prosthetic heart valves react differently to expansion, embodiments hereof are designed to prevent migration of prosthetic heart valves regardless of their structure and construction.

Figure 2:
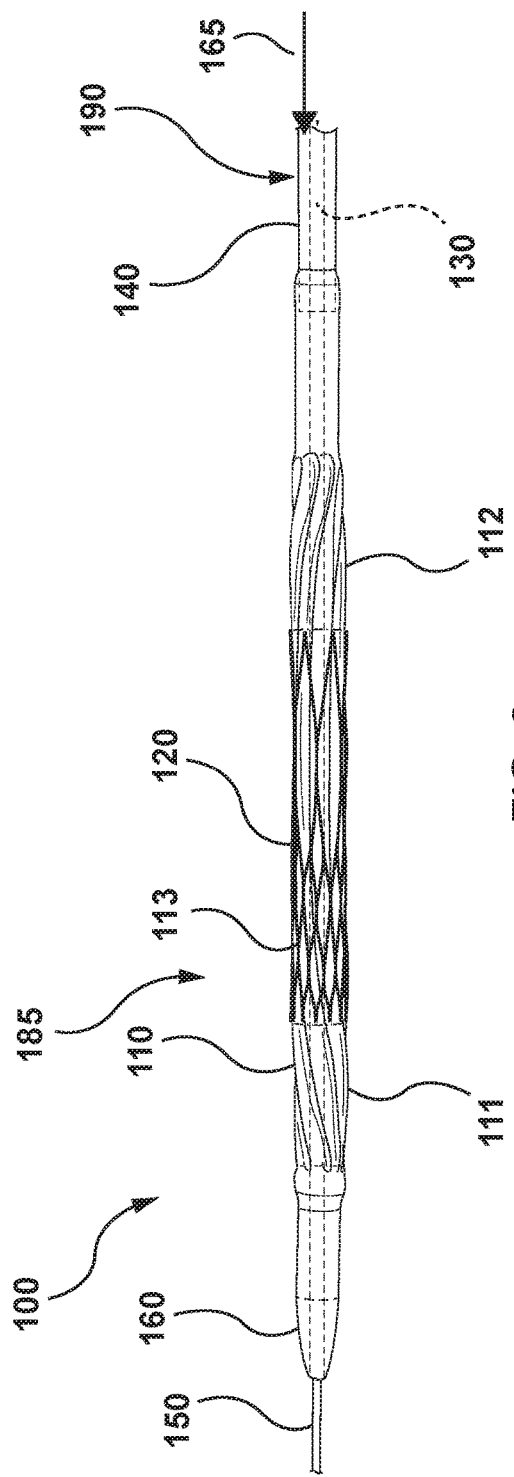
FIG. 2 illustrates a balloon delivery device for prosthetic heart valve deployment.
Figure 3:
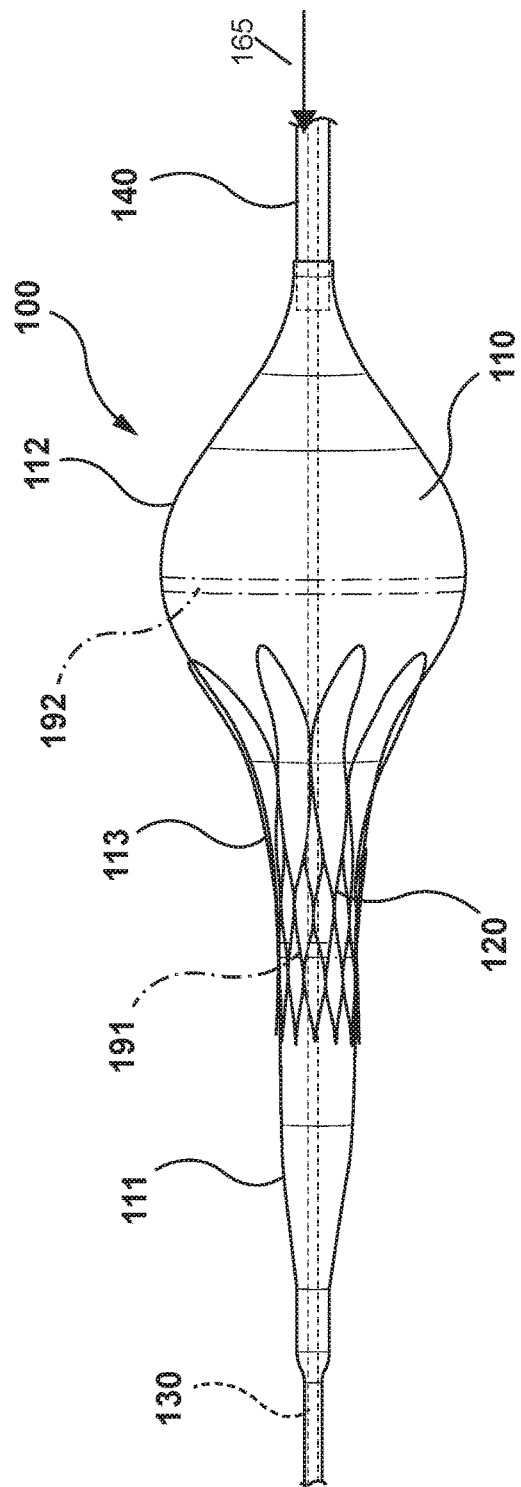
FIG. 3 illustrates partial expansion of a balloon expandable prosthetic heart valve by an expandable balloon delivery device.
Figure 4:
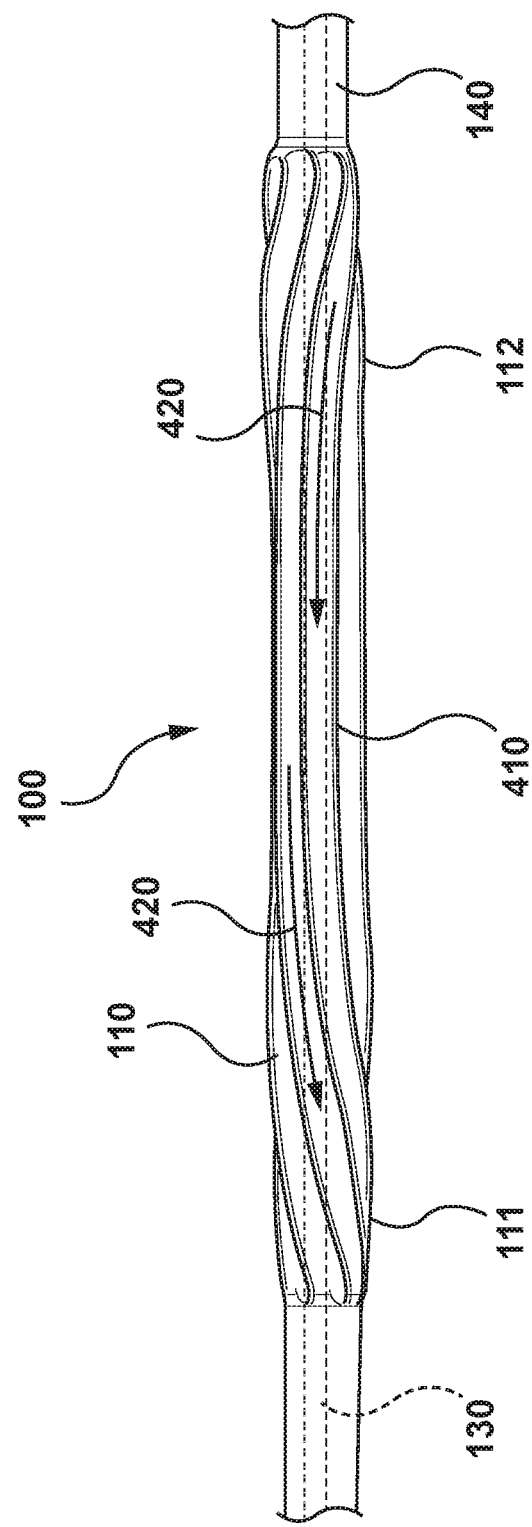
FIG. 4 illustrates a fluid flow path in a balloon delivery device.

FIGS. 2-4 illustrate an expandable balloon delivery device and operation thereof. FIGS. 2-4 provide a detailed description of challenges encountered with some expandable balloon delivery devices.

FIG. 2 illustrates an expandable balloon delivery device for prosthetic heart valve deployment. The expandable balloon delivery device 100 includes an inflatable balloon 110, a prosthetic heart valve 120, an outer shaft 140, and an inner shaft 130. The inner shaft 130 defines a guidewire lumen such that the expandable balloon delivery device 100 may be slidably disposed and tracked over guidewire 150. The outer shaft 140 defines an annular balloon inflation lumen disposed between the inner shaft 130 and the outer shaft 140. The balloon 110 includes a distal portion 111, a proximal portion 112, and a central portion 113. The proximal portion 112 of the balloon 110 is disposed over the outer shaft 140. The outer shaft 140 may be tapered or stepped to a smaller diameter to accommodate the balloon 110. The distal portion 111 of the balloon is retained by the distal tip 160 of the expandable balloon delivery device 100. Both the inner shaft 130 and the outer shaft 140 extend proximally and terminate in a handle or housing (not shown) of the expandable balloon delivery device 100.

The outer shaft 140 extends into the interior of the balloon 110 and terminates therein, while the inner shaft 130, defining the guidewire lumen, extends to the distal tip 160 and terminates therein. This arrangement permits the balloon inflation lumen to carry fluid pumped from the handle of the expandable balloon delivery device 100 into the interior of the balloon 110. The release of fluid to the interior of the balloon 110 causes the balloon 110 to inflate, an action that is employed to expand a prosthetic heart valve frame and deploy the prosthetic heart valve 120, as discussed in greater detail below.

FIG. 3 illustrates partial expansion of a balloon expandable prosthetic heart valve 120 by the expandable balloon delivery device 100. During use, the expandable balloon delivery device 100 is guided to a site of deployment over a guidewire inserted into the guidewire lumen defined by the inner shaft 130. After reaching the site of deployment, the prosthetic heart valve 120 is deployed through balloon expansion. To effect balloon expansion, fluid is delivered to the balloon 110 via the balloon inflation lumen 165 between the outer shaft 140 and the inner shaft 130. As the fluid is delivered, the balloon 110 inflates, causing the expansion of the frame of the prosthetic heart valve 120 that is disposed on the balloon 110. After the balloon 110 fully expands the prosthetic heart valve 120, fluid is removed from the balloon 110 to cause it to deflate. The balloon 110 deflates and the expandable balloon delivery device 100 is withdrawn, leaving the prosthetic heart valve 120 in an expanded and deployed position.

FIG. 3 also illustrates the uneven expansion of the expandable balloon 110, which can occur in the conventional expandable balloon delivery device 100. The uneven expansion, wherein a proximal portion 112 of the balloon inflates at a faster rather than a distal portion 111, may cause movement of the prosthetic heart valve 120 during deployment. Proximal marker 192 and distal marker 191 show the expected positions of the proximal and distal ends of the prosthetic heart valve 120. Uneven expansion of the balloon causes the prosthetic heart valve 120 to migrate along the length of the balloon away from the balloon portion showing more expansion. As shown in FIG. 3, with reference to the proximal marker 192 and distal marker 191, the prosthetic heart valve 120 has migrated away from the larger proximal portion 111 of the balloon 110 and toward the smaller distal portion 112 of the balloon 110. During deployment in the body, such migration may cause the prosthetic heart valve 120 to be deployed at a location that differs from that intended by the operator of the expandable balloon delivery device 100.

FIG. 4 illustrates a fluid flow path in the expandable balloon delivery device 100. The expandable balloon delivery device 100 includes a balloon 110 having pleats 410, an inner shaft 130, and an outer shaft 140. The fluid flow path from the annular balloon inflation lumen between the inner shaft 130 and the outer shaft 140 through the inflation area of the balloon 110 is illustrated by arrows 420. Arrows 420 show the winding fluid flow path, which is obstructed by the pleats 410 of the balloon 110. Because the balloon 110 is folded and compacted into a tight area around the expandable balloon delivery device 100, there is no clear and unobstructed fluid flow pathway from the proximal portion 112 of the balloon 110 to the distal portion 111 of the balloon. When the prosthetic heart valve 120 is crimped atop the balloon 110, the distal portion 111 and the proximal portion 112 extend past the ends of the prosthetic heart valve 120. These portions of the balloon 110 are not restricted by the crimped prosthetic heart valve 120 and will tend to inflate before the prosthetic heart valve 120 begins expansion. However, the obstructed fluid flow pathway results in a pressure differential between the proximal portion 112 and the distal portion 111, which causes the proximal portion 112 to inflate before the distal portion 111, as shown in FIG. 3. This non-uniform expansion can cause the displacement of the prosthetic heart valve 120 during deployment, as shown in and described with respect to FIG. 3.

FIGS. 5-9 illustrate an embodiment of an expandable balloon delivery device 200 that provides improved uniformity of balloon expansion by balancing fluid flow at the proximal and distal portions of the expansion balloon. The embodiment of FIGS. 5-9 prevents migration of a prosthetic heart valve by providing a mechanical lock to maintain or lock an axial position of the prosthetic heart valve. The expandable balloon delivery device 200 is configured so as to expand at proximal and distal portions in a balanced fashion prior to significant expansion in a central portion. The expansion of the proximal and distal portions of the balloon, to diameters larger than that of the crimped prosthetic heart valve, prevents the prosthetic heart valve from migrating either proximally or distally. The flow of inflation fluid to the proximal and distal portions is balanced such that the proximal portion and the distal portion inflate at similar rates, so as to prevent migration caused by unbalanced expansion as shown in FIG. 2.

FIG. 5 is a plan view showing aspects of the expandable balloon delivery device 200. The expandable balloon delivery device 200 includes a distal tip 260, an outer shaft 240, an inner shaft 230, an inflation shaft 270, and a balloon 210. In the proximal portion of the expandable balloon delivery device 200, the outer shaft 240 and the inner shaft 230 define an inflation lumen 265 therebetween. In the distal portion of the expandable delivery device 200, where the inflation shaft 270 is located, the inflation lumen 265 is divided into a first inflation lumen 275 and a second inflation lumen 245 by the inflation shaft 270. The first inflation lumen 275 is defined by the annular lumen between the inflation shaft 270 and the inner shaft 230. The second inflation lumen 245 is defined by the annular lumen between the outer shaft 240 and the inflation shaft 270.

The balloon 210 includes a distal portion 211, a proximal portion 212, and a central portion 213. The end of the proximal portion 212 of the balloon 210 is secured to the outer shaft 240, which terminates inside the proximal portion 212. The inflation shaft 270 extends through the balloon 210 and terminates in the distal tip 260. Thus, the second inflation lumen 245 terminates at the proximal portion 212 of the balloon 210 where the outer shaft 240 terminates while the first inflation lumen 275 extends past the central portion 213 of the balloon 210 and at least to the distal portion 211 of the balloon 210. The proximal end of the inflation shaft 270 may terminate at any point within the outer shaft 240 proximal of the balloon 210 and may also extend proximally throughout the length of the outer shaft 240 to be secured in a handle of the expandable balloon delivery device 200.

FIG. 6 is a cross-sectional view showing aspects of the expandable balloon delivery device 200, taken at the 6-6 cross-sectional line. The inner shaft 230 defines a guidewire lumen 235 therein. The inflation shaft 270 is disposed around the inner shaft 230 and a first inflation lumen 275 is defined therebetween. The outer shaft 240 is disposed around the inflation shaft 270 and a second inflation lumen 245 is defined therebetween. Thus, the larger annular inflation lumen defined between the inner shaft 230 and the outer shaft 240 is divided into the first inflation lumen 275 and the second inflation lumen 245 by the inflation shaft 270.

Figure 7:
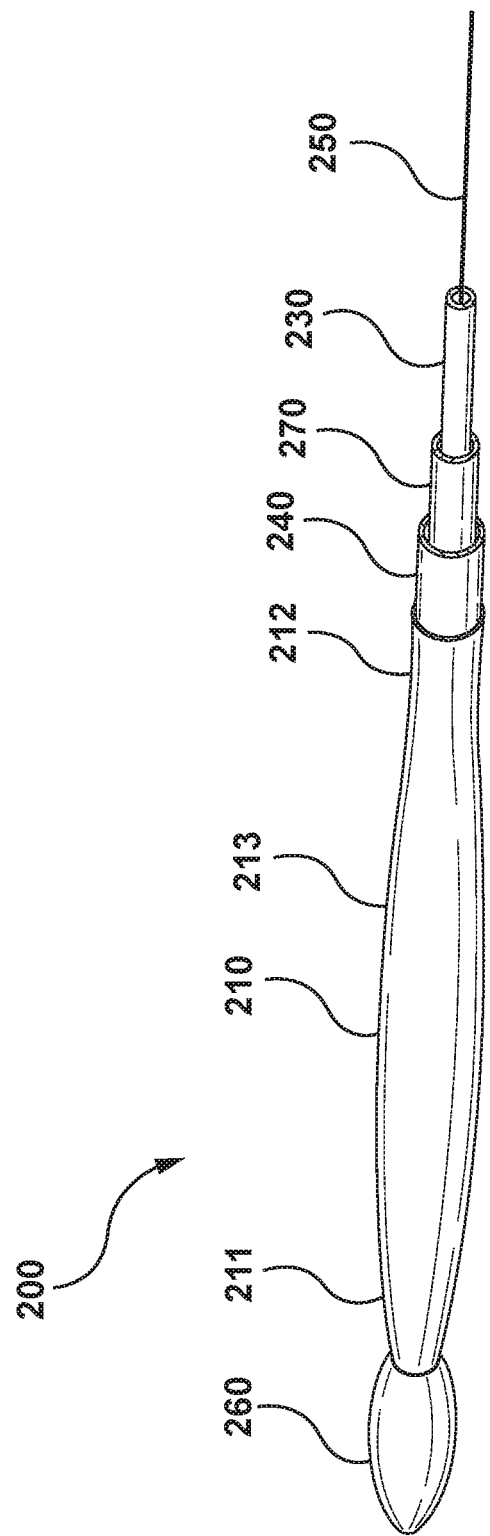
FIG. 7 is a perspective view showing aspects of an expandable balloon delivery device configured to balance fluid flow to proximal and distal portions of a delivery balloon according to embodiments hereof.

FIG. 7 is a perspective view showing aspects of the expandable balloon delivery device 200 configured to balance fluid flow to proximal and distal portions of a delivery balloon. The expandable balloon delivery device 200 includes a distal tip 260, an outer shaft 240, an inner shaft 230, an inflation shaft 270, and a balloon 210. The balloon 210 includes a distal portion 211, a proximal portion 212, and a central portion 213. The expandable balloon delivery device 200 is configured for delivery via a guidewire 250.

Figure 8A:
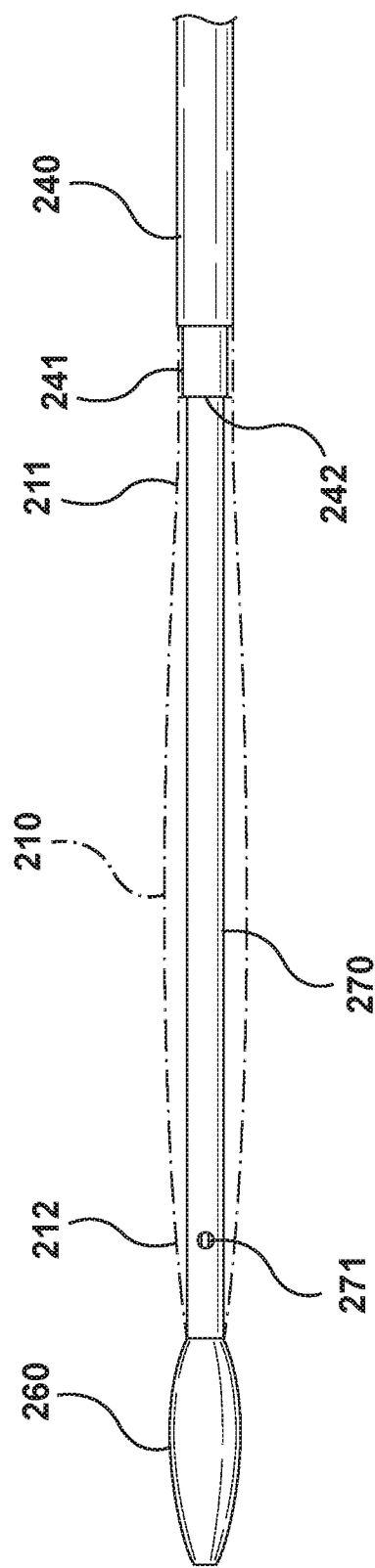
FIGS. 8A and 8B are close-up plan views of an inflation shaft inside an expandable balloon delivery device according to embodiments hereof.
Figure 8B:
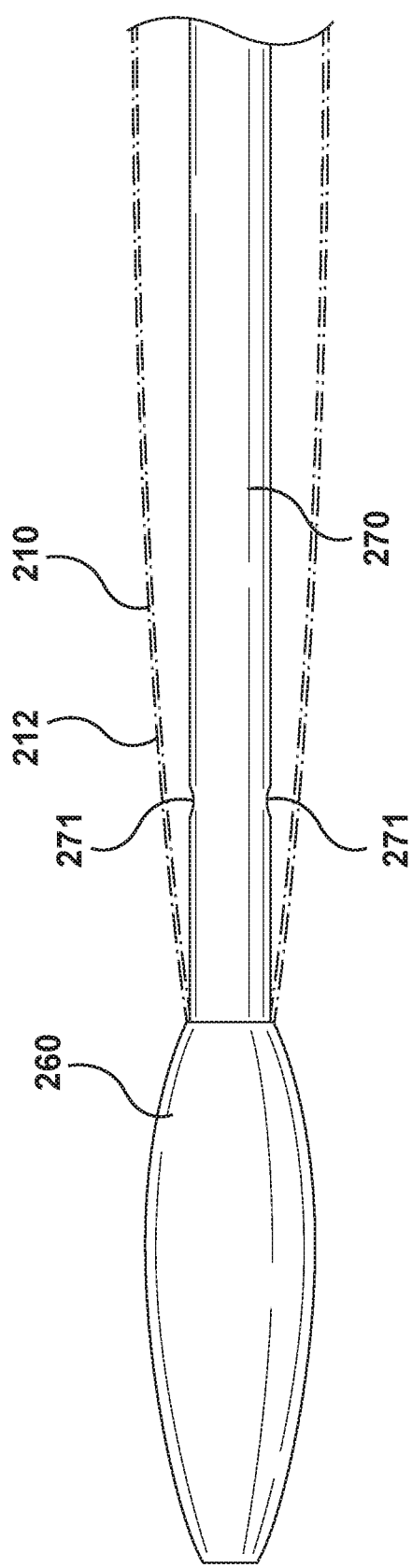

FIGS. 8A and 8B are close-up plan views of the inflation shaft 270 inside the balloon 210. As illustrated in FIG. 8A, the balloon 210 is secured to the outer shaft 240, which terminates inside the proximal portion 212 of the balloon 210. The outer shaft 240 may include a narrowed portion 241 to which the balloon 210 is secured. The narrowed portion 241 has a smaller exterior diameter to the rest of the outer shaft 240 and permits the balloon 210 to be secured to the end of the outer shaft 240 without significant increase to the bulk of the expandable balloon delivery device 200 at that portion. The narrowed portion 241 is not required and the portion of the outer shaft 240 to which the balloon 210 is secured may be the same diameter as the remainder of the outer shaft 240. The outer shaft 240 terminates in a distal opening 242 through which inflation fluid flows to inflate the proximal portion of the balloon. The inflation shaft 270 includes one or more flow holes 271 disposed on the inflation shaft 270 within the distal portion 212 of the balloon 210. FIG. 8A illustrates an embodiment including one flow hole 271 while FIG. 8B illustrates an embodiment including two flow holes 271. In further embodiments, more flow holes 271 may be included, larger or smaller flow holes 271 may be included, and/or different arrangements of flow holes 271 may be included.

In further embodiments, aspects of the expandable balloon delivery device 200 may be altered to enhance the balance of balloon expansion. For example, the fluid flow balance may be adjusted by altering the diameter and/or wall thickness of the inflation shaft 270. The proximal extension length of the inflation shaft 270 may also be adjusted to alter fluid flow balance. Further, the number, size, and shape of the flow holes 271 may be adjusted as required to enhance fluid flow balance.

The inflation shaft 270 may further serve to augment the physical performance of the delivery system. The addition of the inflation shaft 270 may have the effect of increasing the bend and axial stiffness. The properties, i.e., composition, dimension, and construction of the inflation shaft 270 are adjusted to minimize kink points at the transition from the crimped prosthetic heart valve to the adjacent areas of the delivery device. Thus, the inflation shaft 270 has the dual purpose of providing a strain relief and balancing expansion of the balloon.

In the aforementioned embodiments, the inflation shaft 270 is constructed of metal, polymer, or composite structures. Examples of polymers include but are not limited to nylons, PEEK, pebaxes, polyesters, fluorocarbons, polyethylenes and polyurethanes. Examples of metals include but are not limited to stainless steel, MP35N, elgiloy, and L605. Examples of composite structures include but are not limited to metal braid with polymer jacket and liners, metal coils with polymer jacket and liners, polymer braids such as PEEK or Kevlar and polymer jackets and liners and polymer coils such as PEEK or Kevlar and polymer jackets and liners.

The structure of the expandable balloon delivery device 200 is configured to provide balanced fluid flow to the proximal portion 212 and the distal portion 211 of the balloon 210 during deployment of a prosthetic heart valve. Fluid is pumped from the proximal end of the expandable delivery device 200 into the inflation lumen 265 and travels through the inflation lumen 265 until the inflation lumen 265 is split into the first inflation lumen 275 and the second inflation lumen 245. Thereafter, the inflation fluid travels through the first inflation lumen 275 and the second inflation lumen 245. In alternate embodiments, the inflation shaft 270 extends proximally for the entire length of the expandable balloon delivery device 200. In such embodiments, inflation fluid may be initially pumped into the first inflation lumen 275 and the second inflation lumen 245. The first inflation lumen 275, inside the inflation shaft 270, extends past the proximal portion 212 of the balloon 210 and into the distal portion 211 of the balloon 210. Fluid flows through the first inflation lumen 275 and out the flow holes 271 in the distal portion 211 of the balloon 210 to provide inflation pressure at the distal portion 211 of the balloon. The outer shaft 240 and the second inflation lumen 245 terminate at the proximal portion 212 inside of the balloon 210. Fluid flows through the second inflation lumen 245 to provide inflation pressure at the proximal portion 212 of the balloon 210. Fluid from both the first inflation lumen 275 and the second inflation lumen 245 flows from the distal portion 211 and the proximal portion 212, respectively, to provide inflation pressure to the central portion 213 of the balloon 210. Due to the interrupted flow pathways reaching the central portion 213 of the balloon 210 and to the proximal portion 212 and the distal portion 211 being unrestricted by the prosthetic heart valve crimping, the distal portion 211 and the proximal portion 212 of the balloon 210 inflate before the central portion 213 of the balloon 210 and thereby provide a mechanical lock to maintain the axial position of the prosthetic heart valve, as explained in closer detail below with respect to FIGS. 9A-9E.

FIGS. 9A-9E illustrate deployment of a balloon expandable prosthetic heart valve 220 according to an embodiment employing a mechanical lock to maintain the axial position of the prosthetic heart valve 220. The expandable balloon delivery device 200 is configured for the balloon 210 to inflate for deployment of the prosthetic heart valve 220 in stages. In a first stage, fluid for inflation is delivered through the first inflation lumen 275 and the second inflation lumen 245 to provide balanced flow to the proximal portion 212 and the distal portion 211 of the balloon 210. The balanced flow permits the inflation of the proximal portion 212 and the distal portion 211 to provide a mechanical lock to the prosthetic heart valve 220. The mechanical lock prevents the prosthetic heart valve 220 from migrating proximally or distally from its original position, as marked by distal marker arrow 291 and proximal marker arrow 292 (shown in FIG. 9D). In a second stage, fluid for inflation flows from the proximal portion 212 and the distal portion 211 to the central portion 213 to inflate the central portion of the balloon 213 and thereby expand the prosthetic heart valve 220 for delivery. The first stage and the second stage of balloon inflation are not required to be discrete stages and may show overlap as the second stage begins while the first stage is ongoing.

In embodiments, the proximal portion 212 and/or the distal portion 211 of the balloon 210 includes excess material to facilitate the mechanical locking action. The proximal portion 212 and the distal portion 211 of the balloon each extend past the crimped prosthetic heart valve, as shown and discussed below with respect to FIGS. 9A-9E. The balloon 210 may be configured such that the distal portion 211 and the proximal portion 212 includes additional material to facilitate inflation of these portions prior to inflation of the central portion 213. Such additional material may add additional working length to the balloon and/or may increase the diameter of the fully extended balloon at either or both of the proximal portion 212 and the distal portion 211. In further embodiments, the shape of the balloon 210 may be tapered or biased towards either the proximal portion 212 or the distal portion 211.

Figure 9A:
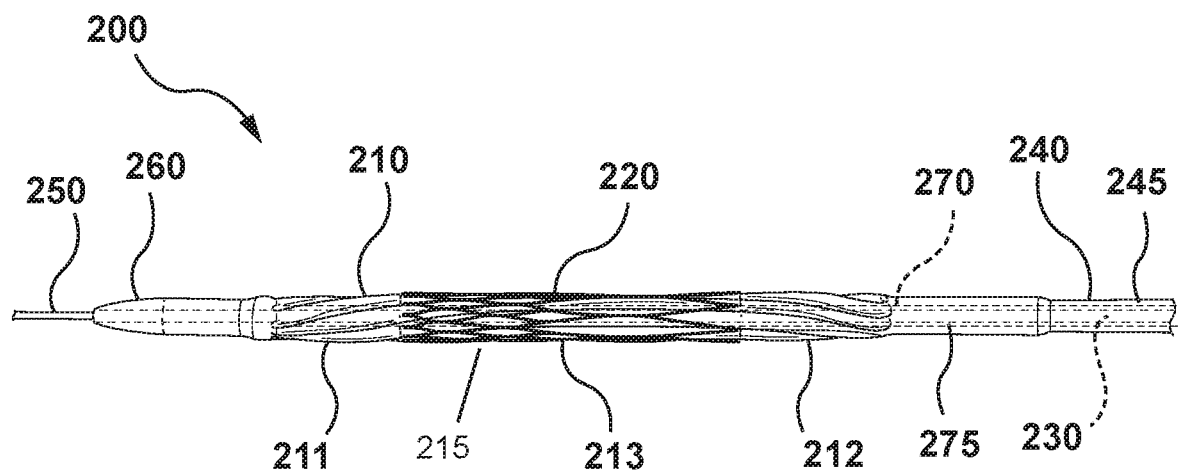
FIGS. 9A-9E illustrate deployment of a balloon expandable prosthetic heart valve according to an embodiment employing a mechanical lock to maintain the axial position of the prosthetic heart valve.

FIG. 9A illustrates the expandable balloon delivery device 200 prior to balloon inflation for deployment of the prosthetic heart valve 220. The balloon 210 is secured to the expandable balloon delivery device 200, with the proximal portion 212 being secured to the outer shaft 240 and the distal portion 211 being secured to the distal tip 260. The prosthetic heart valve 220 is crimped on or otherwise secured over the central portion 213 of the balloon 210. The central portion 213 of the balloon 210 defines a crimping location 215 for the prosthetic heart valve 220 located between a distal portion 211 and a proximal portion 212 of the balloon 210. The distal portion 211 of the balloon 210 extends distally past the crimping location 215 and a proximal portion 212 of the balloon extends proximally past the crimping location 215, leaving the distal portion 211 and the proximal portion 212 free to expand before the prosthetic heart valve 220 expands.

Figure 9B:
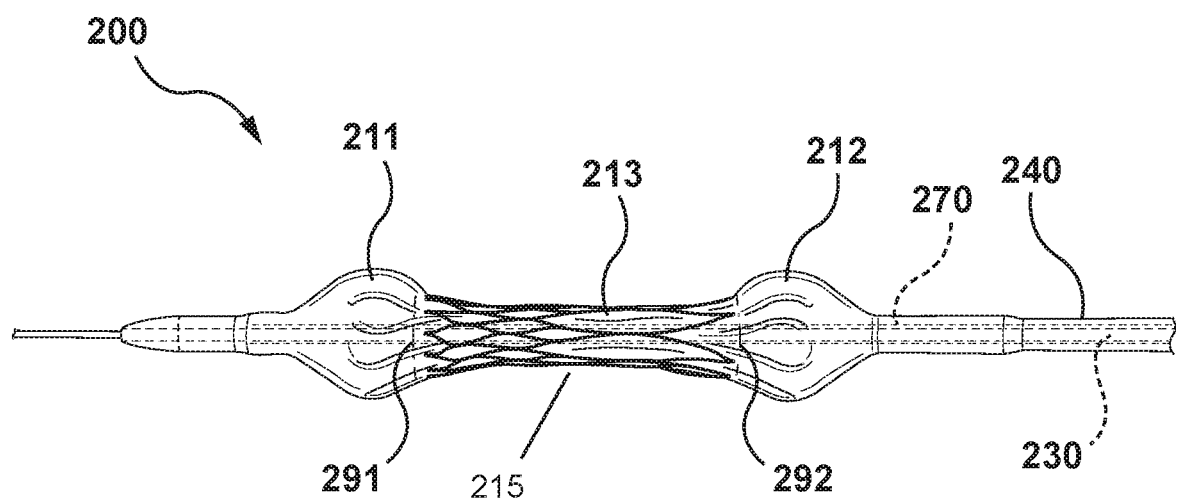

FIG. 9B illustrates the expandable balloon delivery device 200 during a first stage of balloon deployment. Inflation fluid is injected and the proximal portion 212 and the distal portion 211 of the balloon 200 begin to inflate. Due to the flow balancing structure of the expandable balloon delivery device 200, both the proximal portion 212 and the distal portion 211 inflate at a similar rate. The expanded lobes of the proximal portion 212 and the distal portion 211, which are not resisted by the crimping of the prosthetic heart valve 220, serve to mechanically lock the prosthetic heart valve 220 between the proximal portion 212 and the distal portion 211, thus preventing migration during deployment. The prosthetic heart valve 220 cannot move proximally or distally because the expansion of the proximal portion 212 and the distal portion 211 to diameters larger than that of the prosthetic heart valve 220 prevent it.

Figure 9C:
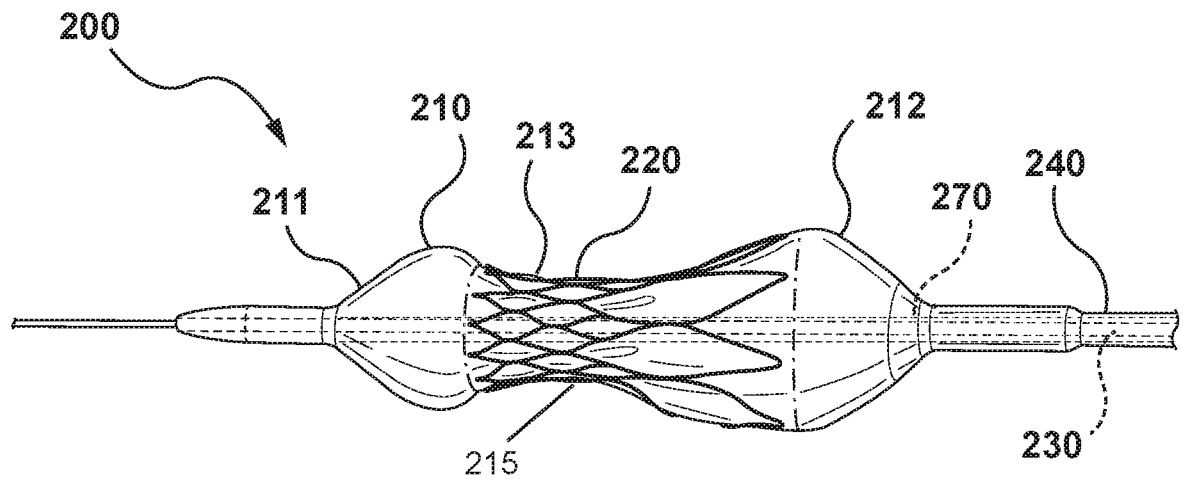

FIG. 9C illustrates the expandable balloon delivery device 200 during a second stage of balloon deployment. During the second stage of balloon deployment, the central portion 213 inflates due to inflation fluid pressure. The inflation of the central portion 213 causes the prosthetic heart valve 220 to begin to expand for deployment. Although the second stage has begun, the first stage is not yet complete, as the proximal portion 212 and the distal portion 211 continue to expand.

Figure 9D:
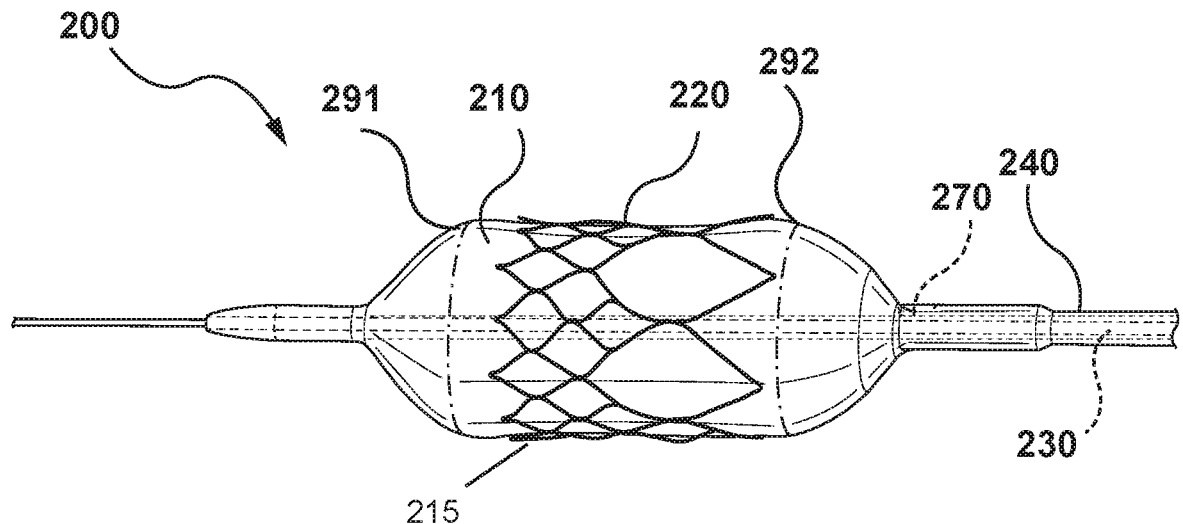
Figure 9E:
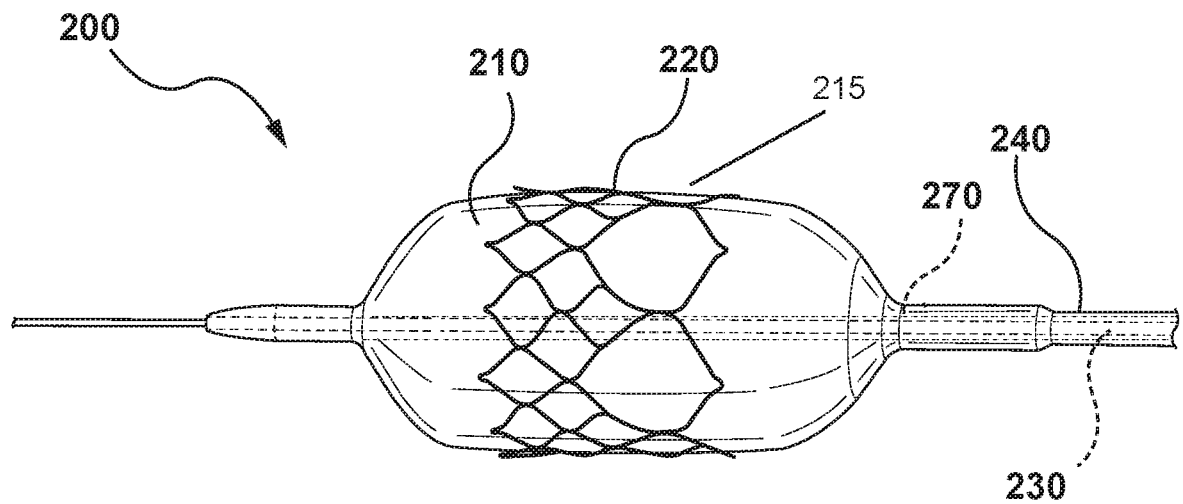

FIGS. 9D and 9E illustrate the continued inflation of the balloon 210 and expansion of the prosthetic heart valve 220 for deployment. As shown in FIG. 9D, the balloon 210 continues to inflate, further expanding the prosthetic heart valve 220. As shown in FIG. 9E, the balloon 210 completes inflation. After expansion of prosthetic heart valve 220, the balloon 210 is deflated by draining the inflation fluid so that the expandable balloon delivery device 200 may be extracted, leaving the deployed prosthetic heart valve 220 in place.

The embodiments illustrated in FIGS. 5-9 for providing balanced expansion of the balloon 210 are illustrative of devices described herein to provide a mechanical lock during the balloon deployment of the prosthetic heart valve 220. As discussed above, the expandable balloon delivery device 200 provides balanced expansion through balancing proximal and distal inflation fluid flow. Variations of the embodiments illustrated in FIGS. 5-9 are described below.

In further embodiments, as illustrated in FIGS. 10-12, the inflation shaft terminates within the distal portion of the balloon.

FIGS. 10A-10B illustrate an expandable balloon delivery device 1000 according to embodiments hereof. The expandable balloon delivery device 1000 includes an inflation shaft 1070, an outer shaft 1040, an inner shaft 1030, a balloon 1010, and a distal tip 1060. The balloon 1010 has a proximal portion 1012 and a distal portion 1011. In this embodiment, the inflation shaft 1070 terminates within the distal portion 1011 of the balloon 1010 rather than terminating in the distal tip 1060. The inflation shaft 1070 includes an open distal end 1071 to permit fluid flow that provides inflation pressure to the distal portion 1011 of the balloon 1010. The outer shaft 1040 includes an open distal end 1041 to permit fluid flow that provides inflation pressure to the proximal portion 1012 of the balloon 110, through the second inflation lumen 1045, as described below. FIG. 10B is a cross-sectional illustration of the expandable balloon delivery device 1000 taken along the cross-section line 10B-10B of FIG. 10A. The inner shaft 1030 defines a guidewire lumen 1035. The inflation shaft 1070 surrounds the inner shaft 1030 and defines a first inflation lumen 1075 between the inflation shaft 1170 and the inner shaft 1130. The outer shaft 1040 surrounds the inflation shaft 1070 and defines the second inflation lumen 1045 between the outer shaft 1040 and the inflation shaft 1070. The inflation shaft 1070 is secured within the outer shaft 1040 by one or more spacers 1049. The one or more spacers 1049 are each secured to the inflation shaft 1070 and to either the inner shaft 1030 or the outer shaft 1040. The spacers 1049 are configured so as not to impede fluid flow, for example as several struts or spokes that extend between the shafts. The spacers 1049 may be placed in the first inflation lumen 1075 or the second inflation lumen 1045, or both. The spacers 1049 may be located anywhere along the length of the inflation shaft 1070. In further embodiments, the expandable balloon delivery device 1000 may include fluid flow holes at a distal end of the inflation shaft 1070. In further embodiments, the inflation shaft 1070 may be tapered to adjust the balance of fluid pressure between the proximal portion 1012 and the distal portion 1011. The expandable balloon delivery device 1000 operates in substantially the same fashion as expandable balloon delivery device 200, except where differences are explicitly described above. Expandable balloon delivery device 1000 may include any and all features of expandable balloon delivery device 200 as discussed above, including fluid flow holes, material selections, and any other feature or aspect not explicitly excluded. Further, the features of the expandable balloon delivery device 1000 may be included in the expandable balloon delivery device 200. The spacers 149 may be employed in the expandable balloon delivery device 200 to maintain the patency of the first inflation lumen 275 and the second inflation lumen 245 even though the inflation shaft 270 is supported by the distal tip 260.

Figure 11A:
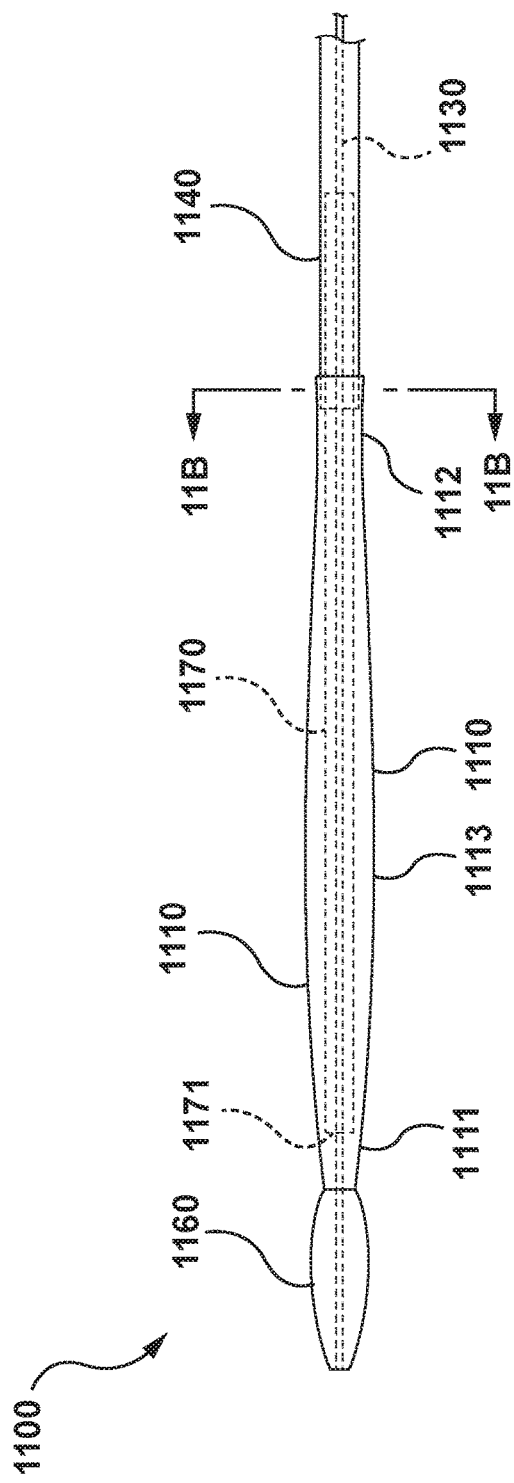
FIGS. 11A-11B illustrate an expandable balloon delivery device according to embodiments hereof.
Figure 11B:
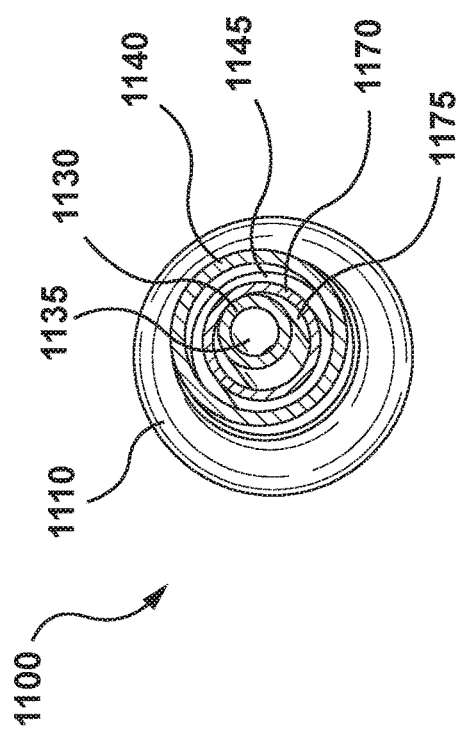

FIGS. 11A-11B illustrate an expandable balloon delivery device 1100 according to embodiments hereof. The expandable balloon delivery device 1100 includes an inflation shaft 1170, an outer shaft 1140, an inner shaft 1130, a balloon 1110, and a distal tip 1160. The balloon 1110 has a proximal portion 1112 and a distal portion 1111. The inflation shaft 1170 terminates within the distal portion 1111 of the balloon 1110 rather than terminating in the distal tip 1160. The end of the inflation shaft 1170 includes an open distal end 1171 to permit fluid flow that provides inflation pressure to the distal portion 1111 of the balloon 1110. Inflation pressure to the proximal portion 1112 of the balloon 1110 is provided by fluid entering the proximal portion 1112 from the outer shaft 1140. FIG. 11B is a cross-sectional illustration of the expandable balloon delivery device 1100 taken along the cross-section line 11B-11B of FIG. 11A. The inner shaft 1130 defines a guidewire lumen 1135. The inflation shaft 1170 surrounds the inner shaft 1130 and defines a first inflation lumen 1175 between the inflation shaft 1170 and the inner shaft 1130. The outer shaft 1140 surrounds the inflation shaft 1170 and defines a second inflation lumen 1145 between the outer shaft 1140 and the inflation shaft 1170. The inflation shaft 1170 is secured to the inner shaft 1130 and is thus eccentrically positioned with respect to the centerline of the expandable balloon delivery device 1100. The inflation shaft 1170 may be secured to the inner shaft 1130, for example, through a bond that extends along all or a portion of the length of the inflation shaft 1170. In further embodiments, the expandable balloon delivery device 1100 may include fluid flow holes at a distal end of the inflation shaft 1170. In further embodiments, the inflation shaft 1170 may be tapered to adjust the balance of fluid pressure between the proximal portion 1112 and the distal portion 1111. The expandable balloon delivery device 1100 operates in substantially the same fashion as expandable balloon delivery device 200, except where differences are explicitly described above. Expandable balloon delivery device 1100 may include any and all features of expandable balloon delivery device 200 as discussed above, including fluid flow holes, material selections, and any other feature or aspect not explicitly excluded.

FIGS. 12A-12B illustrate an expandable balloon delivery device 1200 according to embodiments hereof. FIG. 12A illustrates expandable balloon delivery device 1200, including an inflation shaft 1270, an outer shaft 1240, an inner shaft 1230, a balloon 1210, and a distal tip 1260. The balloon 1210 has a proximal portion 1212 and a distal portion 1211. In this embodiment, the inflation shaft 1270 terminates within the distal portion 1211 of the balloon 1210 rather than terminating in the distal tip 1260. The end of the inflation shaft 1270 includes an open distal end 1271 to permit fluid flow that provides inflation pressure to the distal portion 1211 of the balloon 1210. Inflation pressure to the proximal portion 1212 of the balloon 1210 is provided by fluid entering the proximal portion 1212 from the outer shaft 1240. FIG. 12B is a cross-sectional illustration of the expandable balloon delivery device 1200 taken along the cross-sectional line 12B-12B of FIG. 12A. The inner shaft 1230 defines a guidewire lumen 1235. The inflation shaft 1270 surrounds the inner shaft 1230 and defines a first inflation lumen 1275 between the inflation shaft 1270 and the inner shaft 1230. The outer shaft 1240 surrounds the inflation shaft 1270 and defines a second inflation lumen 1045 between the outer shaft 1240 and the inflation shaft 1270. The inflation shaft 1270 is secured to the outer shaft 1240 and is thus eccentrically positioned with respect to the centerline of the expandable balloon delivery device 1200. The inflation shaft 1270 may be secured to the outer shaft 1240, for example, through a bond that extends along all or a portion of the length of the inflation shaft 1270. In further embodiments, the expandable balloon delivery device 1200 may include fluid flow holes at a distal end of the inflation shaft 1270. In further embodiments, the inflation shaft 1270 may be tapered to adjust the balance of fluid pressure between the proximal portion 1212 and the distal portion 1211. The expandable balloon delivery device 1200 operates in substantially the same fashion as expandable balloon delivery device 200, except where differences are explicitly described above. Expandable balloon delivery device 1200 may include any and all features of expandable balloon delivery device 200 as discussed above, including fluid flow holes, material selections, and any other feature or aspect not explicitly excluded.

Figure 13:
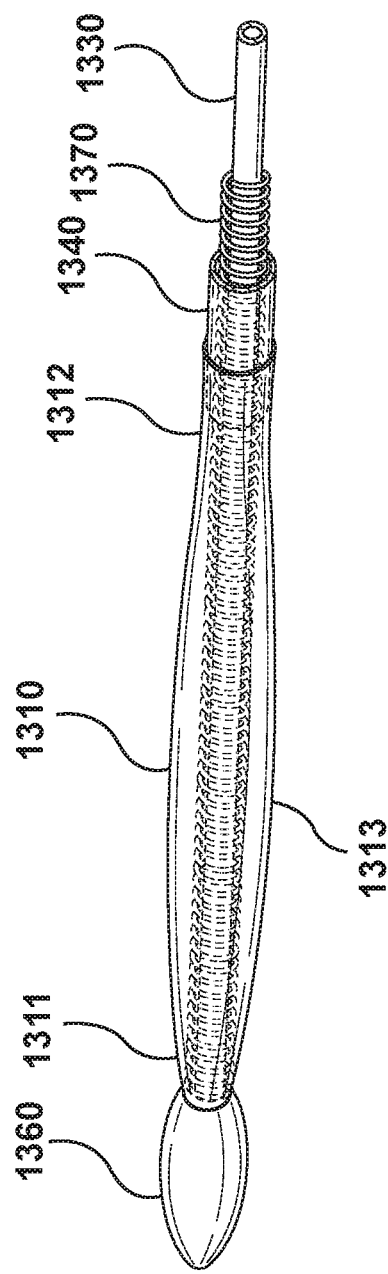
FIG. 13 illustrates an embodiment of an expandable balloon delivery device configured to provide balanced expansion of a prosthetic heart valve deployment balloon according to embodiments hereof.

FIG. 13 illustrates an embodiment of an expandable balloon delivery device 1300 configured to provide balanced expansion of a prosthetic heart valve deployment balloon 1310 according to embodiments hereof. The expandable balloon delivery device 1300 includes a balloon 1310, a distal tip 1360, an outer shaft 1340, an inner shaft 1330, and an inflation support 1370. The inner shaft 1330 and the outer shaft 1340 define an inflation lumen therebetween. The inflation support 1370 is a support structure that ensures a flow channel remains open between the balloon 1310 with a prosthetic valve crimped thereon and the inner shaft 1330. The proximal portion 1312 of the balloon 1310 is secured to the outer shaft 1340, which terminates inside the proximal portion 1312. The inner shaft 1330 continues through the balloon 1310 to the distal tip 1360. The inflation support 1370 extends through the balloon 1310 to a distal portion 1311 of the balloon to maintain a space between the crimped balloon 1310 and the inner shaft 1330, allowing inflation fluid to flow from the proximal portion 1312, through the central portion 1313, and to the distal portion 1311 without significant pressure drop. The open sides of the inflation support 1370 permit fluid to flow out of the open space created by the inflation support 1370 with no hindrance.

In an embodiment, as illustrated in FIG. 13, the inflation support 1370 is a coil constructed of metal or polymer. The coil preserves a lumen beneath the folded balloon to thereby balance flow across the balloon. The coil diameter, pitch, spacing and construction (flat wire, round wire) may be altered to adjust mechanical and flow properties. In another embodiment, the inflation support 1370 is a coil bonded to a polymer shaft. The polymer shaft section extends proximally to the balloon and acts as a flow diverter to split the flow of inflation fluid above and below the coil of the inflation shaft 1370. In yet another embodiment, the inflation support 1370 is a metal or polymer scaffold. The scaffold may be laser cut, for example from hypodermic tubing to create tubular scaffolding with a pattern to allow fluid entry on the proximal end and to exit where desired along the length of the folded balloon 1310.

Figure 14:
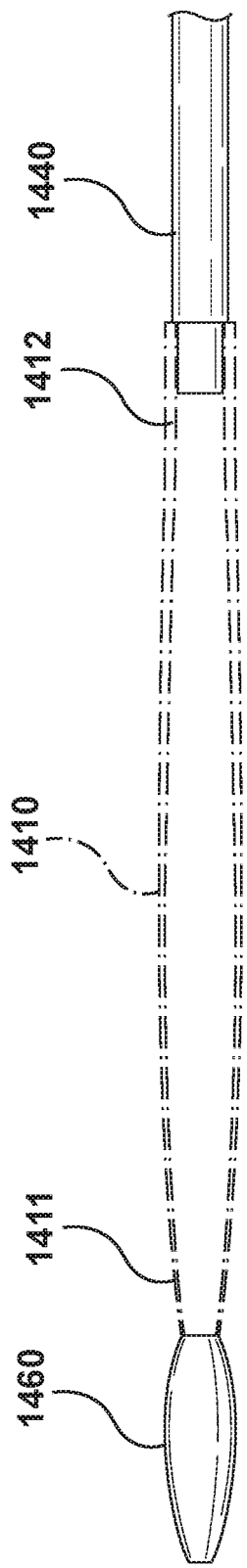
FIG. 14 illustrates an embodiment of an expandable balloon delivery device configured to provide balanced expansion of a prosthetic heart valve deployment balloon according to embodiments hereof.

FIG. 14 illustrates an embodiment of an expandable balloon delivery device 1400 configured to provide balanced expansion of a prosthetic heart valve deployment balloon according to embodiments hereof. The expandable balloon delivery device 1400 includes an outer shaft 1440, an inner shaft 1430, a distal tip 1460, and a balloon 1410. The balloon 1410 has a proximal portion 1412 and a distal portion 1411. In the balloon 1410, balanced expansion is provided by adjusting the resistance to expansion of the balloon from the proximal portion 1412 to the distal portion 1411. The distal portion 1411 of the balloon 1410 has a reduced wall thickness as compared to the proximal portion 1412 of the balloon 1410. The reduced wall thickness serves to reduce the expansion resistance and allow a lower fluid pressure to expand the distal portion 1411. This lower pressure requirement to expand the distal portion 1411 counteracts the flow restrictive effects of the crimped balloon 1410 folds. The altered balloon of this embodiment may be combined with any of the other embodiments discussed herein.

In an alternate embodiment, the distal portion 1411 of the balloon 1410 has an increased wall thickness as compared to the proximal portion 1412 of the balloon 1410. The increased wall thickness serves to increase the expansion resistance and require a higher pressure to expand the distal portion 1411. The higher pressure requirement serves to slow the expansion of the distal portion 1411 as compared to the proximal portion 1410. Although some balloon delivery devices may require expansion restrictions at a proximal end of the balloon, use of balloon 1410 having variable wall thicknesses in combination with other methods and devices described herein, e.g., methods that either deliver additional expansion fluid to a distal end of the balloon 1710 or that otherwise restrict expansion of the proximal portion of the balloon 1710, may make it useful to employ the balloon 1410 with a thickened distal portion 1411 to achieve the desired results. The altered balloon 1410 of this embodiment may be combined with any of the other embodiments discussed herein.

Figure 15:
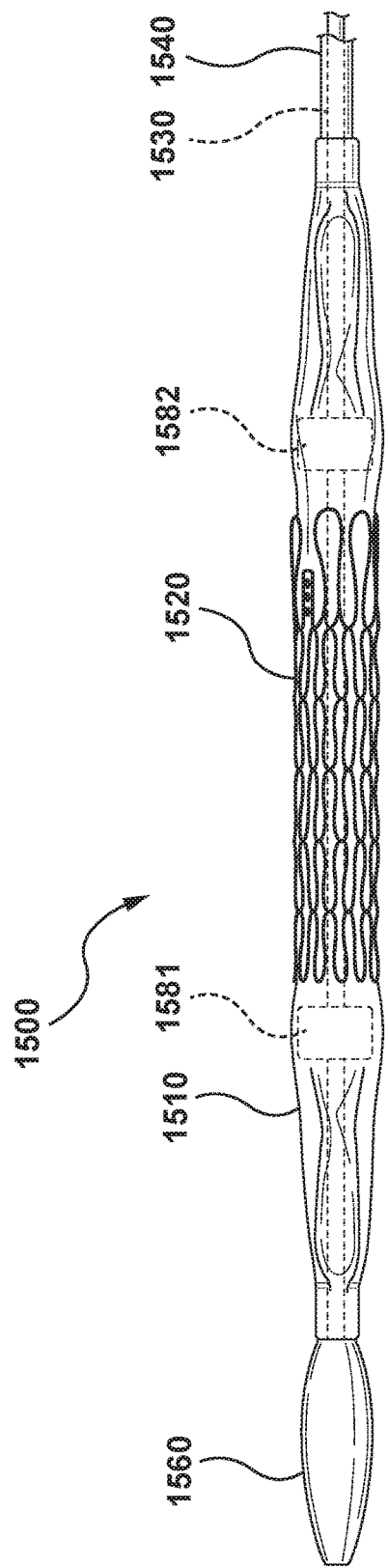
FIG. 15 illustrates an embodiment of an expandable balloon delivery device configured to provide prevent prosthetic heart valve migration during balloon deployment according to embodiments hereof.

FIG. 15 illustrates an embodiment of an expandable balloon delivery device 1500 configured to prevent prosthetic heart valve migration during balloon deployment according to embodiments hereof. Expandable balloon delivery device 1500 includes an outer shaft 1540, an inner shaft 1530, a distal tip 1560, a balloon 1510, a distal retention ring 1581 and a proximal retention ring 1582. The retention rings 1581, 1582 are internal to the balloon and are secured to the inner shaft 1530. During the initial first stage of expansion, the retention rings 1581, 1582 act as a physical stop preventing the prosthetic heart valve from migrating. The retention rings 1581, 1582 are made of, for example, rigid or elastomeric material. The retention rings 1581, 1582 may also be configured to restrict/adjust flow to influence the bias of balloon inflation and/or may have internal features configured so as to permit free flow of inflation fluid. The retention rings 1581, 1582 of this embodiment may be employed to assist in prosthetic heart valve retention in any of the other embodiments discussed herein.

Figure 16:
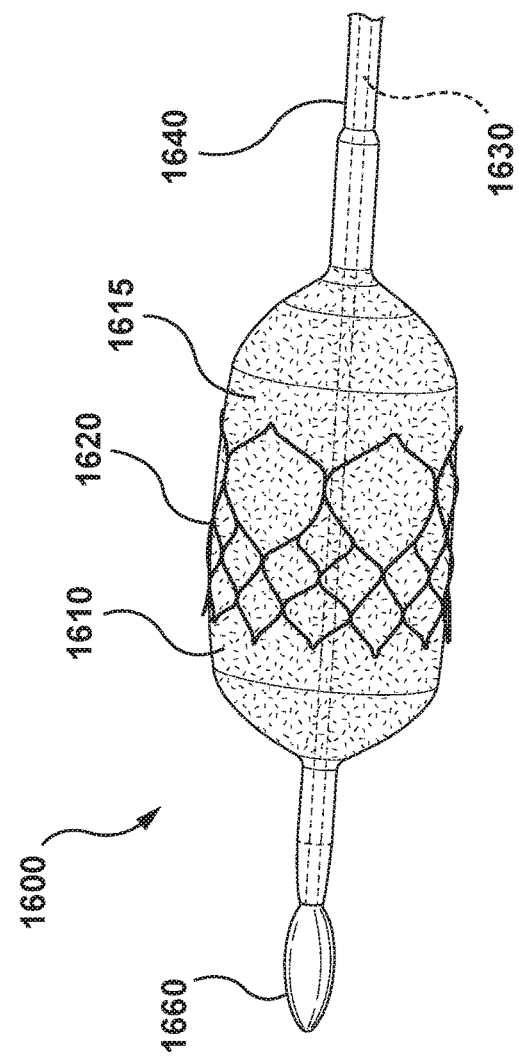
FIG. 16 illustrates an embodiment of an expandable balloon delivery device configured to prevent prosthetic heart valve migration during balloon enabled deployment according to embodiments hereof.

FIG. 16 illustrates another embodiment of an expandable balloon delivery device 1600 configured to prevent prosthetic heart valve migration during balloon enabled deployment. Expandable balloon delivery device 1600 includes a balloon 1610, an inner shaft 1630, and outer shaft 1640, and a distal tip 1660. The balloon 1610 of expandable balloon delivery device 1600 is coated to provide increased friction or attraction between the balloon surface 1615 and the prosthetic heart valve 1620. For example, the balloon surface 1615 may be coated with rubber. In other examples, the balloon surface 1615 is modified to include texture, such as bumps, ridges, and/or protrusions, to increase mechanical locking between the balloon surface 1615 and the prosthetic heart valve 1620 and interfere with any migration of a prosthetic heart valve 1620. The surface texture may interact with the folded valve tissue of the prosthetic heart valve 1620 to create multiple instances of mechanical interlocking. In another example, fine filaments may be added to the balloon surface 1615 to generate electromagnetic or Van der Waals attraction. The fine filaments include filaments of approximately 200 nm in diameter that project from the balloon surface 1615 and cover the portions of the balloon 1610 that require adhesion to the prosthetic heart valve 1620. The filaments may be larger or smaller than 200 nm as required. The filaments are constructed of polymers and create instances of Van der Waals attraction with any surfaces contacting the balloon 1610. Such filaments provide a force that serves to reduce or prevent migration of the prosthetic heart valve 1620 during balloon inflation. The altered balloon of this embodiment may be combined with any of the other embodiments discussed herein.

Figure 17:
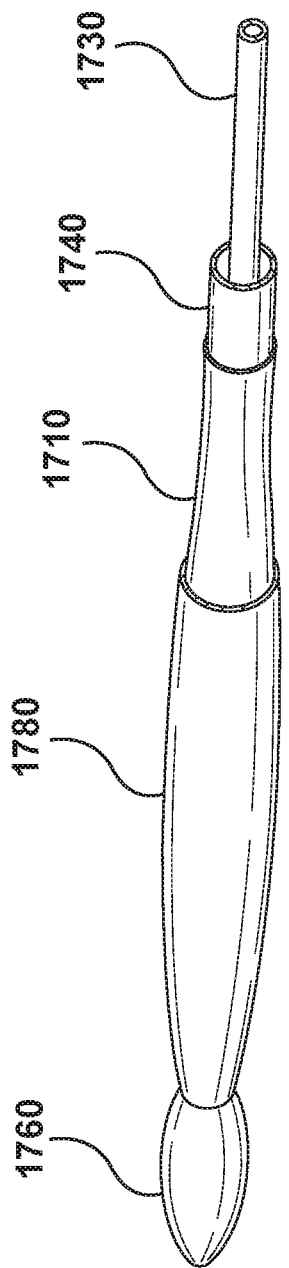
FIG. 17 illustrates an embodiment of an expandable balloon delivery device configured to prevent prosthetic heart valve migration during balloon enabled deployment according to embodiments hereof.

FIG. 17 illustrates another embodiment of an expandable balloon delivery device 1700 configured to prevent prosthetic heart valve migration during balloon enabled deployment. The expandable balloon delivery device 1700 includes an outer shaft 1740, an inner shaft 1730, a balloon 1710, a distal tip 1760, and an expansion cover 1780. The expansion cover 1780 partially covers all or a portion of the balloon 1710 during prosthetic heart valve deployment. The expansion cover 1780 is arranged over all of the balloon 1710 or one end of the balloon 1710 during prosthetic heart valve deployment to reduce or prevent the covered portion of the balloon from expanding.

Features of the expandable balloon delivery device 1700 may be employed with any of the other embodiments and solutions discussed herein. The expansion cover 1780 may be employed to cover the entirety of the balloon 1710 to permit even expansion throughout the length of the balloon before the expansion cover 1780 is retracted. In further embodiments, the expansion cover 1780 may be employed over the proximal or distal portions of the balloon 1710 to balance balloon expansion, depending on which side of the balloon requires additional expansion restrictions. Although some balloon delivery devices may require expansion restrictions at a proximal end of the balloon, use of the expansion cover 1780 in combination with other methods described herein, e.g., methods that either deliver additional expansion fluid to a distal end of the balloon 1710 or that otherwise restrict expansion of the proximal portion of the balloon 1710, may make it useful to employ the expansion cover 1780 over a distal portion of the balloon 1710.

After deployment is begun and the various covered and uncovered portions of the balloon have expanded appropriately, the expansion cover 1780 is retracted to release the covered portion of the balloon 1710 so that the covered end may expand. Preventing expansion is achieved by having the inside diameter of the expansion cover 1780 be a snug fit with the folded balloon outside diameter. Minimizing or reducing expansion is achieved by oversizing the expansion cover 1780 to the folded balloon outside diameter to permit a reduced amount of expansion. As the balloon 1710 is inflated the expansion cover 1780 restricts inflation. The expansion cover 1780 is removed (slid off the balloon 1710) when the desired balloon/prosthetic heart valve inflation/expansion is achieved. The expansion cover 1760 may be arranged over a proximal end, a distal end, a central portion, or an entirety of the balloon 1710. A proximal expansion cover 1780 may be retracted from the balloon 1710 by an extension of the expansion cover 1780 that connects to a handle allowing the user to move the expansion cover 1780. A distal expansion cover 1780 may likewise be connected to a member that travels within the balloon (either in the inflation lumen or other luminal space radially inwards) and be connected to a handle that allows the user to move the member distally. An expansion cover 1780 covering the central portion or the entirety of the balloon may be retracted in either a proximal or distal direction.

Figure 18:
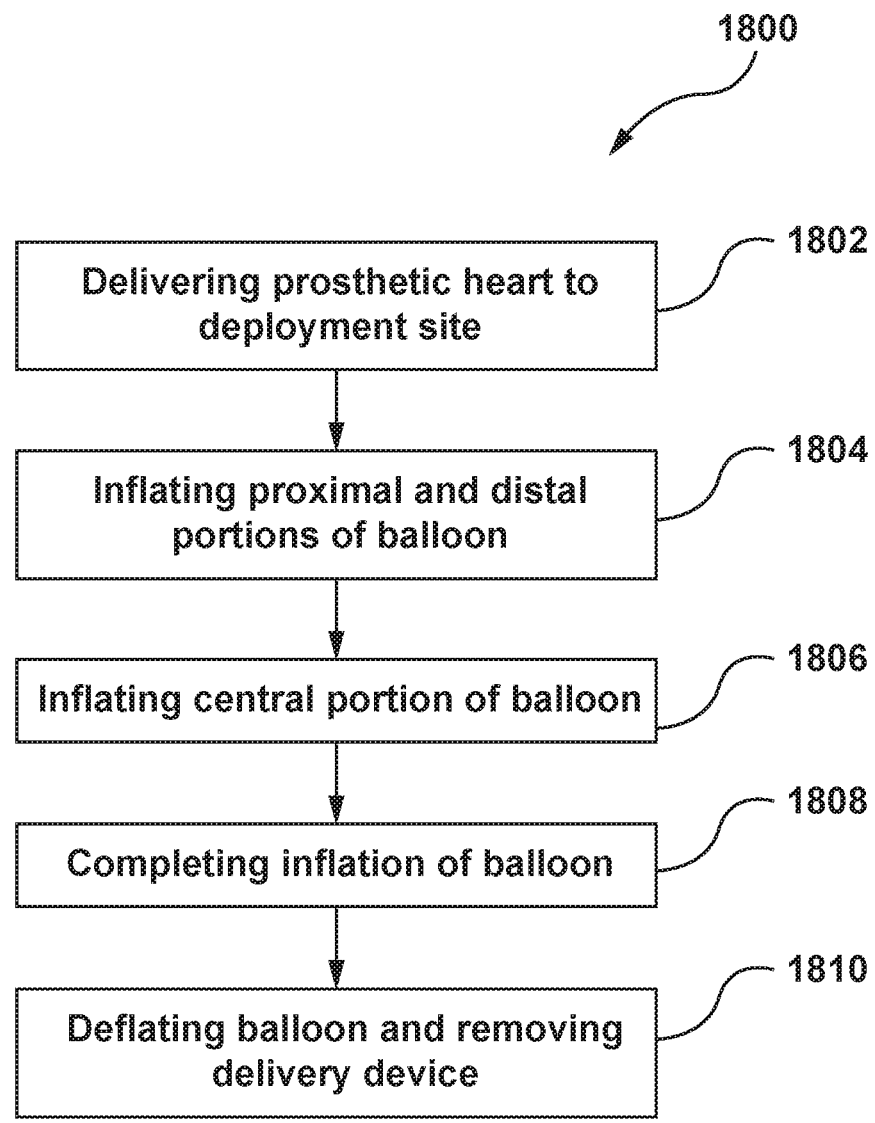
FIG. 18 is a flow chart of a method of balloon deployment of a prosthetic heart valve consistent with embodiments described herein.

FIG. 18 is a flow chart of a method 1800 of balloon deployment of a prosthetic heart valve consistent with embodiments described herein. The devices and structures described herein reduce or prevent prosthetic heart valve migration during balloon deployment. Methods of deploying a prosthetic heart valve to a determined location may be carried out it with any of the embodiments described herein, and with any combination of the embodiments described herein.

In an operation 1802, an expandable balloon delivery device is manipulated to navigate an expandable balloon delivery device catheter tip to a prosthetic heart valve deployment site. The expandable balloon delivery device is navigated through a procedural catheter, a guide catheter, and/or an introducer catheter to deliver the prosthetic heart valve to a site for deployment of the prosthetic heart valve. In some embodiments, the expandable balloon delivery device is delivered via a guidewire that has previously been inserted into the patient vasculature.

In an operation 1804, a first stage of balloon inflation is initiated. Balloon inflation is enabled through pumping pressurized inflation fluid down the length of the expandable balloon delivery device and into the balloon on which the prosthetic heart valve is crimped. Delivery of the inflation fluid is initiated by a user of the system through manipulation of the expandable balloon delivery device handle and/or interaction with a fluid delivery system to which the expandable balloon delivery device is connected. During the first stage of balloon inflation, the proximal and distal portions of the balloon, which extend past the ends of the prosthetic heart valve, inflate to provide a mechanical lock for the prosthetic heart valve. Due to the balloon expansion past the ends of the prosthetic heart valve, the prosthetic heart valve is prevented from migrating either proximally or distally, because the balloon expands to a diameter larger than that of the prosthetic heart valve during the first stage of deployment. Any embodiment or combination of embodiments described herein for balancing flow, balancing expansion, or otherwise providing a mechanical lock.

In an operation 1806, a second stage of balloon inflation is initiated. In the second stage of balloon inflation, a central portion of the balloon inflates to cause expansion and deployment of the prosthetic heart valve. The second stage of balloon inflation may overlap with the first stage and may even begin at the same time as the first stage. The rate of inflation of the central portion of the balloon during the second stage is such that the proximal portion and the distal portion, which extend beyond the edges of the prosthetic heart valve, inflate enough to prevent prosthetic heart valve migration before significant inflation of the central portion. In some embodiments, this may mean that the first stage and second stage are initiated at the same time, with the rate of inflation of the balloon differing between the proximal and distal portions with respect to the central portion. In some embodiments, this may mean that the first stage begins and the proximal and distal portions of the balloon inflate enough to provide the mechanical lock before the second stage of inflation beings. In some embodiments, inflation of the proximal and distal portions may begin before inflation of the central portion and may continue at a higher rate to create the mechanical lock before significant inflation of the central portion begins.

In an operation 1808, inflation of the balloon is continued until the prosthetic heart valve is fully expanded for deployment. Inflation fluid flow to the balloon continues until the prosthetic heart valve has expanded as much as required for positioning within the patient vasculature.

In an operation 1810, the balloon is deflated and the expandable balloon delivery device is removed from the patient. The balloon is deflated through removal of the inflation fluid. The prosthetic heart valve remains in the expanded and deployed position while the expandable balloon delivery device is removed from the local site and from the patient.

The foregoing description has been presented for purposes of illustration and enablement and is not intended to be exhaustive or to limit the invention to the precise form disclosed. Other modifications and variations are possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

What is claimed is:

1. A balloon enabled delivery device for deploying a prosthetic heart valve through balloon inflation, comprising:
an inner shaft defining a guidewire lumen;
an outer shaft surrounding the inner shaft defining an inflation lumen between the outer shaft and the inner shaft;
an inflation shaft disposed between the outer shaft and the inner shaft, wherein a first inflation lumen is defined between the inflation shaft and the inner shaft and a second inflation lumen is defined between the inflation shaft and the outer shaft; and
a balloon disposed at a distal end of the outer shaft such that fluid delivered to the balloon via the first and second inflation lumens cause the balloon to inflate, the balloon having a proximal portion extending proximal of a crimping location of the prosthetic heart valve, a distal portion extending distal of the crimping location, and a central portion located within the crimping location, and being configured to:
inflate in a first stage during which the proximal portion of the balloon is inflated via the second inflation lumen and the distal portion of the balloon is inflated via the first inflation lumen to lock an axial position of the prosthetic heart valve, and
inflate in a second stage during which the central portion of the balloon inflates to expand the prosthetic heart valve.

2. The balloon enabled delivery device of claim 1, further comprising:
a distal tip to which the inflation shaft extends to and terminates at; and
a flow hole located in the inflation shaft and configured to deliver fluid to the distal portion of the balloon.

3. The balloon enabled delivery device of claim 1, further comprising a distal tip to which the inner shaft extends,
wherein the inflation shaft terminates proximal to the distal tip and includes an open distal end through which fluid is delivered to the distal portion of the balloon.

4. The balloon enabled delivery device of claim 3, wherein the inflation shaft is bonded to the inner shaft or the outer shaft for at least a portion of the length of the inflation shaft.

5. The balloon enabled delivery device of claim 3, further comprising a spacer bonded to the inflation shaft and one of the outer shaft or the inner shaft and configured to support the inflation shaft within the outer shaft.

6. The balloon enabled delivery device of claim 1, wherein the inflation shaft is configured to increase the bending stiffness and the axial stiffness of the balloon enabled delivery device.

7. The balloon enabled delivery device of claim 1, further comprising an inflation support disposed between the outer shaft and the inner shaft and configured to maintain a flow pathway from the proximal portion to the distal portion of the balloon.

8. The balloon enabled delivery device of claim 1, wherein a first wall thickness of the proximal portion is greater than a second wall thickness of the distal portion and the balloon is configured to require a lower fluid pressure for the distal portion to inflate.

9. The balloon enabled delivery device of claim 1, further comprising an inflation cover slidably positioned over a portion of the balloon, wherein the portion includes at least one of the proximal portion and the distal portion and is configured to be slidably removed from covering the portion of the balloon.

10. The balloon enabled delivery device of claim 1, further comprising a distal retention ring secured to the inner shaft distal of the crimping location of the prosthetic heart valve and a proximal retention ring secured to the inner shaft proximal of the crimping location of the prosthetic heart valve, wherein the proximal retention ring and the distal retention are configured to prevent migration of the prosthetic heart valve during balloon inflation.

11. The balloon enabled delivery device of claim 1, wherein a balloon surface is treated to reduce migration of the prosthetic heart valve, the balloon surface including at least one of a material configured to increase friction between the balloon surface and the prosthetic heart valve, protrusions configured to interfere with migration of the prosthetic heart valve, and filaments configured to generate an attractive force between the filaments and the prosthetic heart valve.

12. The balloon enabled delivery device of claim 1, further comprising the prosthetic heart valve.

13. A method of deploying a prosthetic heart valve through balloon inflation of a balloon enabled delivery device, comprising:
- advancing the prosthetic heart valve along a guidewire to a deployment site, the guidewire being inserted into a guidewire lumen defined by an inner shaft of the balloon enabled delivery device;
- delivering fluid to a balloon of the balloon enabled delivery device via a first inflation lumen defined between the inner shaft and an inflation shaft surrounding the inner shaft, and a second inflation lumen defined between the inflation shaft and an outer shaft surrounding the inflation shaft;
- inflating a proximal portion of the balloon extending proximal to a crimping location of the prosthetic heart valve via the second inflation lumen;
- inflating a distal portion of the balloon extending distally to the crimping location to lock an axial position of the prosthetic heart valve via the first inflation lumen;
- inflating a central portion of the balloon located within the crimping location of the prosthetic heart valve to expand the prosthetic heart valve;
- completing inflation of the balloon to complete expansion of the prosthetic heart valve; and
- deflating the balloon.

14. The method of claim 13, further comprising delivering the fluid to the distal portion of the balloon through a flow hole located in the inflation shaft.

15. The method of claim 13, further comprising delivering the fluid to the distal portion of the balloon through an open end of the inflation shaft.

16. The method of claim 13, further comprising delivering the fluid to the distal portion of the balloon through a flow pathway maintained by an inflation support disposed between the outer shaft and the inner shaft.

17. The method of claim 13, wherein a first wall thickness of the proximal portion is greater than a second wall thickness of the distal portion and the balloon is configured to require a lower fluid pressure for the distal portion to inflate.

18. The method of claim 13, further comprising restricting inflation of a portion of the balloon via an inflation cover slidably positioned over the portion of the balloon, wherein the portion includes at least one of the proximal portion and the distal portion; and
- slidably removing the inflation cover from the portion of the balloon to permit inflation of the portion.

19. The method of claim 13, further comprising preventing migration of the prosthetic heart valve during balloon inflation via a distal retention ring secured to the inner shaft distal of the crimping location of the prosthetic heart valve and a proximal retention ring secured to the inner shaft proximal of the crimping location of the prosthetic heart valve.

20. The method of claim 13, further comprising reducing migration of the prosthetic heart valve during balloon inflation via a balloon surface treatment, the balloon surface treatment including at least one of a material configured to increase friction between the balloon surface and the prosthetic heart valve, protrusions configured to interfere with migration of the prosthetic heart valve, and filaments configured to generate an attractive force between the filaments and the prosthetic heart valve.

* * * * *